United States Patent [19]

Möller et al.

[11] 4,021,539

[45] May 3, 1977

[54] SKIN TREATING COSMETIC COMPOSITIONS CONTAINING N-POLYHYDROXYALKYL-AMINES

[75] Inventors: Hinrich Möller, Dusseldorf-Benrath; Rainer Osberghaus, Dusseldorf-Urdenbach; Christian Gloxhuber, Haan; Siegfried Braig, Hilden, all of Germany

[73] Assignee: Henkel & Cie G.m.b.H., Dusseldorf-Holthausen, Germany

[22] Filed: Jan. 28, 1975

[21] Appl. No.: 544,859

[30] Foreign Application Priority Data

Jan. 29, 1974 Germany ............ 2404070

[52] U.S. Cl. .......... 424/73; 260/247.5 R; 260/268 R; 260/296 R; 260/584 R; 424/59; 424/74; 424/364; 424/365
[51] Int. Cl.² ............ A61K 7/15; A61K 7/48
[58] Field of Search .... 260/211 R, 584 R, 247.5 R, 260/268 R, 296 R; 424/361, 365, 73, 325

[56] References Cited

UNITED STATES PATENTS

| | | | |
|---|---|---|---|
| 2,703,798 | 3/1955 | Schwartz | 260/211 R |
| 2,715,123 | 8/1955 | Hodge | 260/211 R |
| 2,789,976 | 4/1957 | Zech | 260/211 R |
| 2,808,401 | 10/1957 | Erickson | 260/211 R |
| 2,815,339 | 12/1957 | Erickson | 260/211 R |
| 2,815,340 | 12/1957 | Erickson | 260/211 R |
| 2,922,784 | 1/1960 | Boettner | 260/211 R |
| 2,936,308 | 5/1960 | Hodge | 260/211 R |
| 2,970,128 | 1/1961 | Czendes | 260/42.32 |
| 3,227,616 | 1/1966 | Van Wessem et al. | 424/361 |

FOREIGN PATENTS OR APPLICATIONS 1,816,279  7/1970  Germany

*Primary Examiner*—Albert T. Meyers
*Assistant Examiner*—Vera C. Clarke
*Attorney, Agent, or Firm*—Hammond & Littell

[57] ABSTRACT

The present invention relates to compositions for the treatment of the skin containing up to 25% by weight of at least one N-polyhydroxyalkyl-amine of the formula $$R_1-N-CH-(CHOH)_m-R_2$$
$$\phantom{R_1-N-}|\phantom{CH-(CHO}|$$
$$\phantom{R_1-N}R\phantom{-}(CHOH)_n-H$$

wherein $R_1$ is hydrogen, lower alkyl, hydroxy-lower alkyl or aminoalkyl, as well as heterocyclic aminoalkyl, R is the same as $R_1$ except that both cannot be hydrogen at the same time, $R_2$ is —$CH_2OH$ or —COOH, m is the integer 3 or 4, and n is the integer 0, or, when m is 3 and $R_2$ is —$CH_2OH$, 1; and the method of skin treatment therewith.

9 Claims, No Drawings

SKIN TREATING COSMETIC COMPOSITIONS CONTAINING N-POLYHYDROXYALKYL-AMINES

THE PRIOR ART

It is generally known that protective measures for healthy skin include, among other things, that the skin surface maintains a certain hygroscopicity. If the substances, on which this hygroscopicity and its constant restoration depend, are removed from the skin by environmental influences, such as repeated washing with substances which have a strong wetting and extracting effect, and the influences of chemicals or severe weather, alterations are produced in the horny layer which can greatly reduce the protective action of the skin against harmful environmental influences.

OBJECTS OF THE INVENTION

The object of the present invention is to provide a skin care or skin protection agent, by means of which the functional capacity of the skin may be maintained or increased in spite of harmful environmental influences, and which effectively support the restoration of the horny layer, should any damage have been incurred.

Another object of the present invention is the development of a cosmetic composition for the care and protection of the skin of warm-blooded animals consisting essentially of from 1 to 20% by weight of at least one N-polyhydroxyalkyl-amine compound selected from the group consisting of (1) amines of the formula

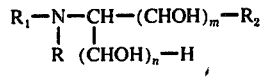

wherein $R_1$ is a member selected from the group consisting of hydrogen, alkyl having from 1 to 18 carbon atoms, hydroxyalkyl having from 2 to 6 carbon atoms, dihydroxyalkyl having from 3 to 6 carbon atoms, trihydroxyalkyl having from 4 to 6 carbon atoms, and

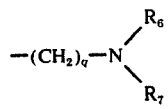

wherein $R_6$ and $R_7$ are members selected from the group consisting of hydrogen, alkyl having from 1 to 12 carbon atoms, hydroxyalkyl having from 1 to 3 carbon atoms, with the proviso that only one of $R_6$ and $R_7$ can be hydrogen, and, when taken together with the nitrogen, pyridyl, piperazino, morpholino, furfuryl, pyrrolidinono and hydroxyalkylpiperazino having from 1 to 3 carbon atoms in the alkyl, and q is an integer from 1 to 3, R is the same as $R_1$, with the proviso that only one of R and $R_1$ can be hydrogen, and R and $R_1$ together with the nitrogen, are alkylpiperazino having from 1 to 3 carbon atoms in the alkyl and hydroxyalkylpiperazino having from 1 to 3 carbon atoms in the alkyl, $R_2$ is a member selected from the group consisting of —$CH_2OH$ and —COOH, m is the integer 3 or 4, and n is the integer 0, or, when m is 3 and $R_2$ is —$CH_2OH$, 1, and (2) physiologically-compatible acid addition salts thereof, and the remainder inert cosmetic excipients.

A further object of the invention is the development of a process for the care and protection of the skin of warm-blooded animals comprising topically applying to the skin a safe but effective amount of the above composition.

A yet further object of the invention is the development of N-polyhydroxyalkyl -amine compounds selected from the group consisting of (1) compounds of the formula

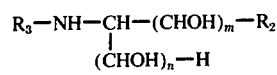

wherein $R_3$ is a member selected from the group consisting of dihydroxyalkyl having 3 to 6 carbon atoms and

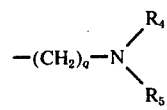

wherein $R_4$ and $R_5$ are members selected from the group consisting of hydrogen, alkyl having from 1 to 3 carbon atoms, hydroxyalkyl having from 1 to 3 carbon atoms, with the proviso that only one of $R_4$ and $R_5$ can be hydrogen, and, when taken together with the nitorgen, pyridyl, morpholino, and piperazino, and q is an integer from 1 to 3, $R_2$ is a member selected from the group consisting of —$CH_2OH$ and —COOH, m is the integer 3 or 4, and n is the integer 0, or, when m is 3 and $R_2$ is —$CH_2OH$, 1, and (2) physiologically-compatible acid addition salts thereof.

These and other objects of the present invention will become more apparent as the description thereof proceeds.

DESCRIPTION OF THE INVENTION

The above objects have been achieved by the discovery of a skin care or skin protection agent comprising conventional constituents such as emulsifiers, fatty substances, plant extracts, solvents, scents, thickeners and preservatives, and from 1 to 20% by weight, preferably 3 to 10% by weight, based on the weight of the whole agent of at least one N-polyhydroxyalkyl-amino of the formula

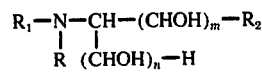

wherein $R_1$ is hydrogen, lower alkyl, hydroxy-lower alkyl or aminoalkyl, as well as heterocyclic aminoalkyl, R is the same as $R_1$ except that both cannot be hydrogen at the same time, $R_2$ is —$CH_2OH$ or —COOH, m is the integer 3 or 4, and n is the integer 0, or, when m is 3 and $R_2$ is $OCH_2OH$, 1; and also containing their acid addition products.

More particularly, the present invention relates to a cosmetic composition for the care and protection of the skin of warm-blooded animals consisting essentially of from 1% to 20% by weight of at least one N-polyhydroxyalkyl-amino compound selected from the group consisting of (1) amines of the formula

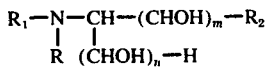

wherein $R_1$ is a member selected from the group consisting of hydrogen, alkyl having from 1 to 18 carbon atoms, hydroxyalkyl having from 2 to 6 carbon atoms, dihydroxyalkyl having from 3 to 6 carbon atoms, trihydroxyalkyl having from 4 to 6 carbon atoms, and

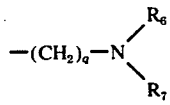

wherein $R_6$ and $R_7$ are members selected from the group consisting of hydrogen, alkyl having from 1 to 12 carbon atoms, hydroxyalkyl having from 1 to 3 carbon atoms, with the proviso that only one of $R_6$ and $R_7$ can be hydrogen, and, when taken together with the nitrogen, pyridyl, piperazino, morpholine, furfuryl, pyrrolidinono and hydroxyalkylpiperazino having from 1 to 3 carbon atoms in the alkyl, and $q$ is an integer from 1 to 3, R is the same as $R_1$ with the proviso that only one of R and $R_1$ can be hydrogen, and R and $R_1$ together with the nitrogen, are alkylpiperazino having from 1 to 3 carbon atoms in the alkyl and hydroxyalkylpiperazino having from 1 to 3 carbon atoms in the alkyl, $R_2$ is a member selected from the group consisting of $-CH_2OH$ and $-COOH$, $m$ is the integer 3 or 4, and $n$ is the integer 0, or, when $m$ is 3 and $R_2$ is $-CH_2OH$, 1, and (2) physiologically-compatible acid addition salts thereof; and the remainder inert cosmetic excipients; as well as a process for the care and protection of the skin of warm-blooded animals comprising topically applying to the skin a safe but effective amount of the above composition. Among the above hydroscopic agents, some are novel compounds, these are N-polyhydroxyalkyl-amine compounds selected from the group consisting of (1) compounds of the formula

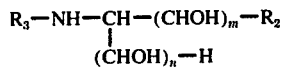

wherein $R_3$ is a member selected from the group consisting of dihydroxyalkyl having 3 to 6 carbon atoms and

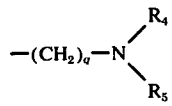

wherein $R_4$ and $R_5$ are members selected from the group consisting of hydrogen, alkyl having from 1 to 3 carbon atoms, hydroxyalkyl having from 1 to 3 carbon atoms, with the proviso that only one of $R_4$ and $R_5$ can be hydrogen, and, when taken together with the nitrogen, pyridyl, morpholino and piperazino, and $q$ is an integer from 1 to 3, $R_2$ is a member selected from the group consisting of $-CH_2OH$ and $-COOH$, $m$ is the integer 3 or 4, and $n$ is the integer 0, or, when $m$ is 3 and $R_2$ is $-CH_2OH$, 1, and (2) physiologically-compatible acid addition salts thereof. In particular, these novel compounds are those where $R_2$ is $-CH_2OH$ and the total of $m+n$ is 4.

The N-polyhydroxyalkyl-amines, which are to be used in accordance with the invention, are produced in a per se known manner by catalytic, reductive amination of monosaccharides or their corresponding uronic acids having from 5 to 6 carbon atoms with amines of the general formula

where R and $R_1$ have the above-assigned values. The catalyst is preferably a hydrogenation catalyst, such as palladium on activated carbon or copper chromite or, in particular, Raney nickel. Preferred solvents are alcohols, ethers, cyclic ethers, oligo ethers, and their mixtures with water. More particularly, the solvents are preferentially alkanols having 1 to 3 carbon atoms, alkanediols having 2 to 4 carbon atoms, alkanetriols having 3 to 5 carbon atoms, dioxane, tetrahydrofuran, polyoxyalkylene glycols having 2 to 3 carbon atoms in the alkylene and 1 to 3 ether oxygen atoms and their mixtures with water. The reaction is carried out at a temperature of between 50° and 100° C. The molar ratio of monosaccharide or its corresponding uronic acid to amine is 1 to 1.2:1. From the reaction products, the N-polyhydroxyalkyl-amine compounds can be recovered by distilling off the solvent and possibly recrystallizing from an alkanol/water mixture.

For the manufacture of the compounds which are used in accordance with the invention a solution of hexoses, pentoses or the corresponding uronic acids in alcohols, cyclic ethers or oligo ethers or their mixtures with water are reductively aminated at a temperature between 50° to 100° C in the presence of hydrogenation catalysts under a hydrogen pressure of 15 to 200 kg/cm² with amines of the general formula

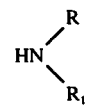

wherein R and $R_1$ have the above-mentioned meaning, in the molar ratio of monosaccharide or uronic acid to amine 1 to 1.2:1. The reaction solutions, after removal by filtration of the catalyst, are evaporated and the N-polyhydroxyalkyl-amine compounds obtained are possibly recrystallized from an alkanol/water mixture.

Suitable hexoses, pentoses or uronic acids for the manufacture of the compounds in accordance with the invention are for example glucose, mannose, gluose, galactose, fructose, sorbose, xylose, arabinose, ribose, glucuronic acid, galacturonic acid and mannuronic acid.

Examples of amines which are suitable for the production of the compounds which are to be used in accordance with the invention are methylamine, ethylamine, propylamine, isopropylamine, hexylamine, dodecylamine, 3-dimethylaminopropylamine, 3-diethylaminopropylamine, 3-octylaminopropylamine, ethanolamine, 2-hydroxypropylamine, 3-hydroxypropylamine, 2,3-hydroxypropylamine, 1,3-dihydroxy-2-methyl-2-amino-propane, 1,3-dihydroxy-2-ethyl-2-aminopropane, α,α,α-trishydroxymethyl-methylamine, 3-[di-(β-hydroxyethyl)-amino]-propylamine, N-(β-hydroxyethyl)ethylenediamine, 3-(β-hydroxyethyl-amino)-propylamine, 2-(β-hydroxyethylamino)-ethylamine, 2-aminoethyl-pyridine, 4-aminomethyl-pyridine, 2-(β-aminoethyl)-pyridine, N-(β-aminoethyl)-piperazine, 4-(3-amino-propyl)-1-(β-hydroxyethyl)-piperazine, N-(β-hydroxyethyl)-piperazine, N-(3-aminopropyl)-piperazine, N-(β-aminoethyl)-morpholine, N-(3-aminopropyl)-morpholine, furfurylamine, N-(3-amino-propyl)-2-pyrrolidone.

Examples of compounds which are to be used in accordance with the invention, amongst them a large number of new products are, for example, N-methylglucamine, N-(β-hydroxyethyl)-glucamine, N-propylglucamine, N-(2-hydroxypropyl)-glucamine, N-(3-dimethylaminopropyl)-glucamine, N-hexylglucamine, N-(3-octylaminopropyl)-glucamine, N-dodecylglucamine, N-(2,3-dihydroxypropyl)-glucamine, N-[3-(di-β-hydroxyethylamino)-propyl]-glucamine, N-(2-pyridyl-methyl)-glucamine, N-(4-pyridyl-methyl)-glucamine, N-(β-2-pyridylethyl)glucamine, N-(β-piperazinoethyl)-glucamine, N-(β-morpholino-ethyl)-glucamine, N-(1,3-dihydroxy-2-methyl-2-propyl)-glucamine, N-[2-(β-hydroxyethylamino)-ethylamino]-glucamine, N-(3-dimethylaminopropyl)-glucamine, N-(3-hydroxypropyl)-glucamine, N-(1,3-dihydroxy-2-ethyl-2-propyl)-glucamine, N-(3-diethylaminopropyl)-glucamine, N-(β-piperazino-hydroxyethyl)-glucamine, and in addition reaction products of D-fructose with 1-(β-aminoethyl)-piperazine, 3-dimethylamino-propylamine, N-(β-hydroxyethyl)-ethylene-diamine, 1,3-dihydroxy-2-methyl-2-propylamine, 3-di-(β-hydroxyethyl)-amino-propylamine, N-(3-aminopropyl)-2-pyrrolidone, 4-(3-aminopropyl)-1-(β-hydroxyethyl)-piperazine, reaction products of D-galactose with N-(3-amino-propyl)-morpholine, 3-(β-hydroxyethylamino)-propylamine, 2-(β-aminoethyl)-pyridine, N-(β-hydroxyethyl)-piperazine, reaction products of D-mannose with N-(β-aminoethyl)-morpholine, α,α,α-trishydroxymethyl-methylamine, N-(β-aminoethyl)-piperazine, 2-(β-hydroxyethylamino)-ethylamine, reaction products of D-xylose with 3-amino-1,2-propanediol, 3-dimethylaminopropylamine, N-(3-aminopropyl)-piperazine, reaction products of D-ribose with 3-[di-(β-hydroxyethyl)-amino]-propylamine, 1,3-dihydroxy-2-ethyl-2-propylamine, 2-(β-hydroxy-ethylamino)-ethylamine, reaction products of D-glucuronic acid with 1-(β-aminoethyl)-piperazine, 3-(β-hydroxyethylamino)propylamine, 2,3-dihydroxy-2-methyl-2-propylamine and reaction products of D-galacturonic acid with α,α,α-trishydroxymethyl-methylamine, 3-dimethylamino-propylamine, etc.

All the acids to which no objections can be raised on physiological grounds, such as hydrochloric acid, phosphoric acid, acetic acid, glycolic acid, lactic acid, propionic acid, succinic acid, malic acid, tartaric acid, citric acid, adipic acid, can be used as acid component for the acid addition products of the N-polyhydroxyalkylamines.

The compounds which are to be used in accordance with the invention are crystalline, wax-like or resin-like substances which range from colorless to pale yellow or pink and are characterized by their good water absorption capacity and also by their excellent water retention capacity. Owing to these properties and their good physiological compatibility they are highly suitable as skin humectants in cosmetic preparations, in particular in agents for the care and protection of the skin.

For this application in cosmetic preparations a special purification or processing of the reaction products obtained after the removal by filtration of the hydrogenation catalyst and removal of the solvent by distillation is not required.

It is known that in addition to other factors a certain hygroscopicity is necessary for the protection of a healthy skin. If the skin is deprived of the substances which are responsible for this hydroscopicity as well as its continual restoration by environmental circumstances such as repeated washings, effect of chemicals or strong weather influences, alterations occur in the stratum corneum, as a result of which the protective effect of the skin against harmful influences of the environment may be considerably diminished.

It was found that the functional capacity of the skin may be maintained or restored even to a higher degree than before if it is treated with agents for the care and protection of the skin, which besides the customary constitutents include from 1 to 20% by weight, preferably 3 to 10% by weight, based on the total composition of the N-polyhydroxyalkyl-amine compounds in accordance with the invention.

It is well known that by themselves, monosaccharides may be added to skin preparations. The advantage of the agents for the care and protection of skin having a content of the N-polyhydroxyalkyl-amine compounds in accordance with the invention over the known agents consists in their deep penetration into the skin and in their ability to keep the skin moist and elastic due to their excellent water absorption and water retention capacity, so that the skin can exercise to an increased degree its natural protective action. A further advantage of the agents for the care and protection of the skin in accordance with the invention is their color stability, even when they are stored for a considerable period of time.

Among the compositions for the care and protection of the skin having special skin-caring properties due to the addition of the N-polyhydroxyalkyl-amine compounds in accordance with the invention or their acid addition salts with physiologically-compatible acids are emulsions of oil-in-water or water-in-oil type. These are the conventional day creams, night creams and nourishing creams, skin protection creams, glycerol creams, creams with special additives of animal or vegetable origin, sun protection or sun tanning creams, and sun protection emulsions, face lotions and after-shave lotions. The incorporation of the agents for care and protection of the skin may take place in the known manner by simple stirring-in or dissolving. In addition to the N-polyhydroxyalkyl-amine compounds in accordance with the invention, the cosmetic preparations may contain the constituents normally present in them such as emulsifiers, fatty substances, plant extracts, preservatives, perfumes, solvents, thickeners and preservatives in the customary amounts. The pH value of the agents for the care and protection of the skin may be in the acid to neutral region (pH 5 – 7.0) and is approximately adjusted to weakly acid values of about pH 6.

The following examples are intended to illustrate the subject of the invention without, however, limiting it to these examples.

EXAMPLES

In the first place, the manufacture of some of the N-polyhydroxyalkyl-amine compounds in accordance with the invention are described below.

EXAMPLE A

N-(2,3-dihydroxypropyl)-glucamine

A solution of 19.6 gm (0.2 mol) of D-glucose (containing 0.1 mol of $H_2O$) and 18.2 gm (0.2 mol) of 2,3-dihydroxypropylamine in 400 ml of water and 350 ml of methanol was, after the addition of 18 gm of Raney nickel, hydrogenated for 2 hours at 50° C in an autoclave having stirring means, and then for 3 hours at 70° C, both at a hydrogen pressure of about 180 kg/cm. After the catalyst had been filtered off and the solvent removed by distillation under reduced pressure, the residue was recrystallized from water/2-propanol and digested with cold 2-propanol. 36.5 gm (72% of theory) of colorless, crystalline N-(2,3-dihydroxypropyl)-glucamine with a melting point of 133° to 134° C was obtained.

The following compounds were obtained in corresponding manner:

EXAMPLE B

N-methyl-glucamine

The product was made from D-glucose and methylamine comparable as in Example A. A crystallized colorless product with a melting point of 127° to 128° C was obtained.

EXAMPLE C

N-($\beta$-hydroxyethyl)-glucamine

The product was made from D-glucose and monoethanolamine comparable as in Example A. A viscous, syrupy substance was obtained.

EXAMPLE D

N-propyl-glucamine

The product was made from D-glucose and n-propylamine comparable as in Example A.

EXAMPLE E

N-(2-hydroxypropyl)-glucamine

The product was made from D-glucose and 2-hydroxypropylamine comparable as in Example A.

EXAMPLE F

N-(3-dimethylamino-propyl)-glucamine

The product was made from D-glucose and 3-dimethylamino-propylamine comparable as in Example A. A colorless, crystalline product with a melting point of 107° to 108° C was obtained.

EXAMPLE G

N-hexyl-glucamine

The product was made from D-glucose and n-hexylamine comparable as in Example A.

EXAMPLE H

N-(3-octylamino-propyl)-glucamine

The product was made from D-glucose and 3-octylamino-propylamine comparable as in Example A.

EXAMPLE J

N-dodecyl-glucamine

The product was made from D-glucose and dodecylamine comparable as in Example A.

EXAMPLE K

N-[3-(di-$\beta$-hydroxyethylamino)-propyl]-glucamine

The product was made from D-glucose and 3-[di-($\beta$-hydroxyethyl)-amino]-propylamine comparable as in Example A. A resin-like, colorless product was obtained.

EXAMPLE L

N-(2-pyridyl-methyl)-glucamine

The product was made from D-glucose and 2-aminomethyl-pyridine comparable as in Example A. A resin-like, yellow product was obtained.

EXAMPLE M

N-(4-pyridyl-methyl)-glucamine

The product was made from D-glucose and 4-aminomethyl-pyridine comparable as in Example A. A resin-like, yellow product was obtained.

EXAMPLE N

N-($\beta$-2-pyridyl-ethyl)-glucamine

The product was made from D-glucose and 2-($\beta$-aminoethyl)-pyridine comparable as in Example A. A wax-like, colorless product was obtained.

EXAMPLE O

N-($\beta$-piperazino-ethyl)-glucamine

The product was made from D-glucose and N-($\beta$-aminoethyl)-piperazine comparable as in Example A. A resin-like, pale pink product was obtained.

EXAMPLE P

N-($\beta$-morpholino-ethyl)-glucamine

The product was made from D-glucose and N-($\beta$-aminoethyl)-morpholine comparable as in Example A. A resin-like, colorless product was obtained.

EXAMPLE Q

N-(1,3-dihydroxy-2-methyl-2propyl)-glucamine

The product was made from D-glucose and 1,3-dihydroxy-2-methyl-2-amino-propane comparable as in Example A. A resin-like, colorless product was obtained.

EXAMPLE R

N-[2-($\beta$-hydroxyethyl-amino)-ethyl]-glucamine

The product was made from D-glucose and N-($\beta$-hydroxyethyl)-ethylenediamine comparable as in Example A. A wax-like, colorless product was obtained.

In order to obtain the acid addition products of the N-polyhydroxyalkyl-amines, it is sufficient to mix their aqueous solutions with the equimolar quantities of the appropriate acid, to which no objection can be raised on physiological grounds, and, if need be, to condense under vacuum. For many purposes, the aqueous solutions of the N-polyhydroxyalkyl-amines or of their acid addition products can be used as they are.

The determination of the water absorption capacity of the compounds in accordance with the invention took place by measuring the increase in weight during storage at 100% relative atmospheric moisture over a certain period of time, usually 48 hours. This was reported as mg water absorbed per 100 mg substance.

The water retention capacity was determined by measuring the residual water content of a moistened sample after storage at 0% relative moisture under a pressure of 12 mm Hg during a period of 45 minutes, 1 ½ hours and 8 hours. The moistening was made with 300 mg H₂O per 100 mg substance. The residual water content was reported as mg of water per 100 mg of compound. The measured values listed in the following Table I were obtained.

5 minutes in warm water of 60° C, the epidermis is then peeled off and stored at −20° C until used.

b. Determination of the water retention and the rehydration of impregnated pig epidermis.

Stamped out pieces of epidermis (1 × 2 cm) were soaked for 2 hours in a 10% solution of the test substance, excess moisture was removed by means of a

TABLE I

Water retention and water absorption capacity of N-polyhydroxyalkyl-amine compounds.

| | Water retention in mg/100 mg substance | | | |
|---|---|---|---|---|
| Product | After 45 minutes | After 90 minutes | After 8 hours | Water absorption in mg/100 mg substance after 48 hours. |
| A | 28.2 | 14.6 | 6.8 | 98.8 |
| B | — | 34.8 | — | 180.4 |
| C | — | 22.2 | 9.6 | 177.1 |
| E | — | 60.0 | 43.0 | 124.0 |
| F | — | 24.5 | 14.2 | 168.1 |
| K | 20.3 | 13.3 | 7.3 | 132.9 |
| L | — | — | — | 80.1 |
| M | 14.3 | 9.8 | — | 42.3 |
| N | — | — | — | 66.7 |
| O | 22.7 | 17.5 | 12.1 | 148.5 |
| P | 14.2 | 9.6 | 5.2 | 128.1 |
| Q | 14.0 | 11.3 | 5.8 | 108.7 |
| R | 14.2 | 5.4 | — | 69.3 |

"—" = was not measured.

The above Table indicates, beside the stong hygroscopicity, also the remarkable water retention capacity of the compounds in accordance with the invention.

The favorable action of the compounds, which are to be used in accordance with the invention, with regard to capacity for the absorption and retention of water, was also determined by means of test methods which are described more fully hereinafter. A process for determining the equilibrium dampness, which constitutes a gauge for the water retention capacity, and the determination of the water retention, rehydration and elasticity of impregnated pig epidermis is described in these tests.

1. Determination of the equilibrium dampness

The substances (about 300 to 500 mg) to be tested were moistened with a defined quantity of water and exposed for 24 hours at 23° to various relative atmospheric humidities (1, 30, 47, 65, 89 and 100% relative humidity). The amount of water absorbed or desorbed was determined gravimetrically and plotted on a graph. The relative humidity at which neither expulsion nor retention of water is effected, can be determined from the resultant curves. This value, which is designated as the equilibrium dampness, is a gauge for the water retention capacity of a substance. The lower the value, the more positive should be the assessment of the product. The steepness of the curve, in addition, indicated the water retaining capacity (hygroscopicity) of the substance.

The values are reported in Table II.

2. Tests on the pig epidermis (a) To obtain the pig epidermis

As soon as the pigs have been killed, the bristles of the skin are cut off by means of a shearing machine (shearing head of 0.1 mm). The pigs are soaked for 3 to 5 minutes in warm water of 60° C, the epidermis is then peeled off and stored at −20° C until used.

small press under standardized conditions and the pieces were dried for 24 hours, hanging free between 2 clamps in a 100 ml Erlenmeyer flask at 23° C both at 30% relative humidity and 50% relative humidity (set by sulfuric acid/water mixtures). The drying out of the impregnated test pieces to X% of the initial weight was compared with the corresponding value of the epidermis which had been soaked only in water (blank value). In Table II, the improvement in the water retention and the rehydration as compared with the blank value is given in Δ% of H₂O. The deviations in each double test amounted to a maximum of ± 2 absolute units. If greater deviations occured, the test was repeated. The rehydration was determined analogously by drying the pig epidermis, which had been impregnated and from which the excess moisture had been removed, for 24 hours at 30% relative humidity, and by subsequent 24-hour incubation at 90% relative humidity.

c. Gauging of elasticity of impregnated pig epidermis

Stamped out pieces of pig epidermis (1 × 6 cm) were soaked for 2 hours in a 10% aqueous solution of the substance which was to be tested, and excess moisture was removed from these pieces under standardized conditions. The test pieces were incubated for 24 hours, hanging free between 2 clamps both at 75% relative humidity and at 90% relative humidity and were stretched in a nipping tensile-testing machine (type: 1402) with 0 to 50 pund loading. The amount of stretch, which was measured in the Hooke range with loadings of 5 to 30 pund, was given in mm as a gauge for the elasticity.

The measured values obtained in the previously described tests can be seen hereinafter in Table II. Care must be taken that solutions of acid addition products of the N-polyhydroxyalkyl-amines with a pH of 6 are used for the tests of the pig epidermis, while the N-polyhydroxyalkylamine compounds are used as they are for the determination of the equilibrium dampness.

TABLE II

Equilibrium dampness and measured values for pig epidermis

| Product | Equilibrium dampness (% r.h.) | Water retention Δ% H₂O after drying out at 30% r.h. | Water retention Δ% H₂O after drying out at 50% r.h. | Rehydration Δ% water absorption at 90% r.h. | mm stretch with between 5 and 30 pund loading at 90% r.h. | mm stretch with between 5 and 30 pund loading at 75% r.h. |
|---|---|---|---|---|---|---|
| Blank value | — | 0 | 0 | 0 | 0.3–0.5 | 0 |
| A | 70 | — | — | — | 1.5 | 0.8 |
| 6% B 4% lactic acid | 89 | 2 | 0 | 6 | — | — |
| 6.7% C 3.3% lactic acid | 78 | 5 | 0 | 4 | — | — |
| 6.7% E 3.3% lactic acid | 91 | 6 | 3 | 5 | — | — |
| 5.3% F 4.7% lactic acid | 79 | 10 | 14 | 17 | — | — |
| F+HCl(pH 6) | 79 | 10 | 13 | 19 | 2.4 | 0.5 |
| K | 76 | — | — | — | 2.1 | 0.4 |
| 6.1% M 3.9% lactic acid | 89 | 11 | 5 | 16 | — | — |
| M+HCl(pH 6) | 89 | 8 | 16 | 42 | 1.9 | 1.0 |
| 6.1% N 3.9% lactic acid | 87 | 7 | 5 | 13 | — | — |
| N+HCl(pH 6) | 87 | 12 | 19 | 42 | 2.2 | 0.5 |
| 6.2% O 3.8% lactic acid | 66 | 3 | 10 | 13 | — | — |
| O+HCl(pH 6) | 66 | 8 | 21 | 40 | 4.5 | 1.2 |
| 6.4% P 3.6% lactic acid | 68 | 6 | 8 | 14 | — | — |
| P+HCl(pH 6) | 68 | 17 | 11 | 39 | 1.5 | 0.5 |
| 6.4% Q 3.6% lactic acid | 63 | 12 | 10 | 22 | — | — |
| Q+HCl(pH 6) | 63 | 20 | 21 | 32 | 1.4 | 1.0 |
| 6% R 4% lactic acid | 80 | 11 | 12 | 5 | — | — |
| R+HCl(pH 6) | 80 | 12 | 12 | 35 | 2.8 | 0.7 |
| 6.12 L 3.9% lactic acid | 81 | 10 | 16 | 14 | — | — |
| L+HCl(pH 6) | 81 | 5 | 20 | 39 | 1.0 | 0.5 |

"—"=was not measured.

These afore-mentioned measured values of Table II also confirm the suitability of the products which are to be used in accordance with the invention as skin moisture-containing agents in skin care and skin protection agents.

In the following, we will give a few examples of cosmetic preparations containing substances in accordance with the invention as skin humectants.

EXAMPLE 1

| Day cream, slightly greasy | Parts by weight |
|---|---|
| Fatty acid partial glyceride Cutina MD Dehydag | 6.0 |
| Stearic acid | 8.0 |
| Mixture of nonionic emulsifiers Emulgin C 700 Dehydag | 3.0 |
| 2-octyl-dodecanol | 4.0 |
| Vegetable oil | 3.0 |
| Paraffin oil | 5.0 |
| Triethanolamine | 0.4 |
| 1,2-propylene glycol | 3.0 |
| Product F, as the lactic acid addition compound | 3.0 |
| Nipagin M, an antimicrobial | 0.2 |
| Perfume oil | 1.0 |
| Water | 63.4 |

EXAMPLE 2

| Baby cream | Parts by Weight |
|---|---|
| Mixture of higher molecular esters, mainly mixed esters of pentaerythritol fatty acid ester and citric acid fatty alcohol ester Dehymuls E Dehydag | 7.0 |
| Decyl oleate | 10.0 |
| Vaseline, a mixture of pasty hydrocarbons | 10.0 |
| Wool fat | 5.0 |
| Boric acid | 0.2 |
| Talcum | 12.0 |
| Zinc oxide | 8.0 |
| Nipagin M | 0.2 |
| Product O, as the lactic acid addition compound | 5.0 |
| Water | 42.6 |

EXAMPLE 3

| Night cream | Parts by Weight |
|---|---|
| Colloidally dispersed mixture of 90 parts of cetyl-stearyl alcohol and 10 parts of sodium lauryl sulfate | 10.0 |
| 2-Octyl-dodecanol | 12.0 |
| Vegetable oil | 7.0 |

-continued

| Night cream | Parts by Weight |
|---|---|
| Wool fat | 2.0 |
| Glycerol | 1.0 |
| Product Q, as the lactic acid addition compound | 5.0 |
| Nipagin M | 0.2 |
| Perfume Oil | 1.0 |
| Water | 61.8 |

EXAMPLE 4

| Boro-glycerol cream | Parts by Weight |
|---|---|
| Colloidally dispersed mixture of 90 parts of cetyl-stearyl alcohol and 10 parts of sodium lauryl sulfate | 12.0 |
| 2-Octyl-dodecanol | 8.0 |
| Vegetable oil | 5.0 |
| Boric acid | 2.0 |
| Glycerol | 28.0 |
| Nipagin M | 0.2 |
| Product P, as the hydrochloric acid addition compound | 3.0 |
| Water | 41.8 |

EXAMPLE 5

| Sun protection cream | Parts by Weight |
|---|---|
| Mixture of higher molecular esters with fatty substances Dehymuls K Dehydag | 30.0 |
| Decyl oleate | 15.0 |
| Light protection agent | 5.0 |
| Nipagin M | 0.2 |
| Product C, as the lactic acid addition compound | 3.0 |
| Water | 46.8 |

EXAMPLE 6

| Face mask | Parts by Weight |
|---|---|
| Mixtures of fatty acid partial glyceride with emulsifiers Cutina LE Dehydag | 12.0 |
| Decyl oleate | 4.0 |
| Vitamin oil | 5.0 |
| Kaolin | 2.0 |
| Rice starch | 3.0 |
| Nipagin M | 0.2 |
| Product O, as the hydrochloric acid addition compound | 6.0 |
| Water | 67.8 |

EXAMPLE 7

| After-shave lotion | Parts by Weight |
|---|---|
| Oleyl/cetyl alcohol | 1.0 |
| Ethanol 96% | 67.5 |
| Menthol | 0.2 |
| Camphor | 0.2 |
| Peru balsam | 0.1 |
| Perfume | 0.5 |
| Hamamelis extract | 10.0 |
| Boric acid | 0.5 |
| Product R, as the hydrochloric acid addition compound | 10.0 |

-continued

| After-shave lotion | Parts by Weight |
|---|---|
| Water | 10.0 |

EXAMPLE 8

| Face lotion | Parts by Weight |
|---|---|
| Cucumber essence | 15.0 |
| Citric acid | 0.2 |
| Ethanol 96% | 15.0 |
| Product L, as the lactic acid addition compound | 10.0 |
| Perfume | 1.0 |
| Water | 58.8 |

In place of the compounds in accordance with the invention mentioned in the above examples, others of the products in accordance with the invention may be used with equally good success.

The preceding specific embodiments are illustrative of the practice of the invention. It is to be understood, however, that other expedients known to those skilled in the art, or given herein, may be employed without departing from the spirit of the invention or the scope of the appended claims.

We claim:

1. A cosmetic composition for maintaining or restoring a certain hygroscopicity in the skin for the protection of the skin of warm-blooded animals consisting essentially of an aqueous composition having a pH of between 5 and 7 and containing from 1 to 20% by weight of at least one N-polyhydroxyalkyl-amine compound selected from the group consisting of (1) amines of the formula

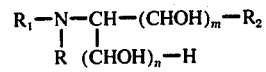

wherein $R_1$ is a member selected from the group consisting of hydrogen, alkyl having from 1 to 18 carbon atoms, hydroxyalkyl having from 2 to 6 carbon atoms, dihydroxyalkyl having from 3 to 6 carbon atoms, trihydroxyalkyl having from 4 to 6 carbon atoms, and

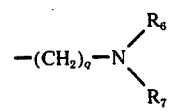

wherein $R_6$ and $R_7$ are members selected from the group consisting of hydrogen, alkyl having from 1 to 12 carbon atoms, hydroxyalkyl having from 1 to 3 carbon atoms, with the proviso that only one of $R_6$ and $R_7$ can be hydrogen, and, when taken together with the nitrogen, pyridyl, piperazino, morpholino, furfuryl, pyrrolidino and hydroxyalkylpiperazino having from 1 to 3 carbon atoms in the alkyl, and $q$ is an integer from 1 to 3, R is the same as $R_1$, with the proviso that only one of R and $R_1$ can be hydrogen, and R and $R_1$ together with the nitrogen, are alkylpiperazino having from 1 to 3 carbon atoms in the alkyl or hydroxyalkylpiperazino having from 1 to 3 carbon atoms in the alkyl, $R_2$ is a member selected from the group consisting of —CH$_2$OH and —COOH, $m$ is the integer 3 or 4, and $n$ is the integer 0, or, when $m$ is 3 and R$_2$ is —CH$_2$OH, 1, and (2) physiologically-compatible acid addition salts thereof, and the remainder to 100% by weight of inert cosmetic excipients.

2. The composition of claim 1 wherein said at least one N-polyhydroxyalkyl-amine compound is present in an amount of from 3 to 10% by weight.

3. The composition of claim 1 wherein R is hydrogen.

4. The composition of claim 1 wherein the pH is 6.

5. The composition of claim 1 wherein said aqueous composition is an aqueous emulsion including an emulsifier.

6. The composition of claim 1 wherein said aqueous composition is an after-shave lotion.

7. A process for maintaining or restoring a certain hygroscopicity in the skin for the protection of the skin of warm-blooded animals comprising topically applying to the skin a safe but effective amount as a moisturizing agent of the composition of claim 1.

8. A cosmetic composition for maintaining or restoring a certain hygroscopicity in the skin for the protection of the skin of warm-blooded animals consisting essentially of an aqueous composition having a pH of between 5 and 7 and containing from 1% to 20% by weight of at least one N-polyhydroxyalkyl-amine compound selected from the group consisting of (1) amines of the formula

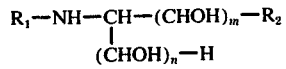

wherein R$_1$ is a member selected from the group consisting of alkyl having from 1 to 18 carbon atoms, hydroxyalkyl having from 2 to 6 carbon atoms, dihydroxyalkyl having from 3 to 6 carbon atoms, trihydroxyalkyl having from 4 to 6 carbon atoms, and

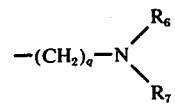

wherein R$_6$ and R$_7$ are members selected from the group consisting of hydrogen, alkyl having from 1 to 12 carbon atoms, hydroxyalkyl having from 1 to 3 carbon atoms, with the proviso that only one of R$_6$ and R$_7$ can be hydrogen, and $q$ is an integer from 1 to 3, R$_2$ is a member selected from the group consisting of —CH$_2$OH and —COOH, $m$ is the integer 3 or 4, and $n$ is the integer 0, or, when $m$ is 3 and R$_2$ is —CH$_2$OH, 1, and (2) physiologically-compatible acid addition salts thereof, and the remainder to 100% by weight of inert cosmetic excipients.

9. The composition of claim 8 wherein said N-polyhydroxyalkyl-amine compound is N-(3-dimethylaminopropyl)-glucamine.

* * * * *